United States Patent
Chang et al.

(10) Patent No.: US 12,396,681 B2
(45) Date of Patent: Aug. 26, 2025

(54) WEARABLE DEVICE

(71) Applicant: Advanced Semiconductor Engineering, Inc., Kaohsiung (TW)

(72) Inventors: Yu-Jung Chang, Taoyuan (TW); Ming-Tau Huang, Taoyuan (TW)

(73) Assignee: ADVANCED SEMICONDUCTOR ENGINEERING, INC., Kaohsiung (TW)

( * ) Notice: Subject to any disclaimer, the term of this patent is extended or adjusted under 35 U.S.C. 154(b) by 1107 days.

(21) Appl. No.: 17/219,562

(22) Filed: Mar. 31, 2021

(65) Prior Publication Data

US 2022/0313163 A1 Oct. 6, 2022

(51) Int. Cl.
*A61B 5/00* (2006.01)
*A61B 5/25* (2021.01)
*H04R 1/10* (2006.01)

(52) U.S. Cl.
CPC .............. *A61B 5/6817* (2013.01); *A61B 5/25* (2021.01); *H04R 1/1016* (2013.01); *A61B 2562/0215* (2017.08); *A61B 2562/164* (2013.01)

(58) Field of Classification Search
CPC . A61B 5/6817; A61B 5/25; A61B 2562/0215; A61B 2562/164; H04R 1/1016
See application file for complete search history.

(56) References Cited

U.S. PATENT DOCUMENTS

| | | | |
|---|---|---|---|
| 10,835,145 B1* | 11/2020 | Prevoir | A61B 5/6817 |
| 10,860,114 B1* | 12/2020 | Oommen | G06F 3/017 |
| 2011/0182457 A1* | 7/2011 | Tung | H04R 1/1041 381/380 |
| 2015/0335288 A1* | 11/2015 | Toth | A61B 5/388 600/391 |
| 2019/0380597 A1 | 12/2019 | Newton | |
| 2020/0107110 A1* | 4/2020 | Ji | H04B 1/385 |
| 2021/0169391 A1* | 6/2021 | Garcia Molina | A61B 5/6817 |

FOREIGN PATENT DOCUMENTS

JP 2011217986 A * 11/2011

OTHER PUBLICATIONS

Ando, H, Translation of JP 2011217986, Nov. 4, 2011 (Year: 2011).*

* cited by examiner

*Primary Examiner* — Adam Z Minchella
(74) *Attorney, Agent, or Firm* — FOLEY & LARDNER LLP

(57) ABSTRACT

The present disclosure provides a wearable device. The wearable device includes a first element and a second element. The first element is configured to sense a bio-signal from a user. The second element is configured to transmit the bio-signal to a processor. The second element has a first surface and a second surface non-coplanar with the first surface. The first element is in contact with the first surface and the second surface of the second element.

17 Claims, 12 Drawing Sheets

WEARABLE DEVICE

BACKGROUND

1. Technical Field

The present disclosure generally relates to a wearable device.

2. Description of the Related Art

Monitoring biologically-relevant information helps determine a wide array of an individual's physiological characteristics. Integrating a monitoring device (such as a sensor) with a wearable device (such as an earpiece) allows pertinent information to be collected in a continuous and non-intrusive manner, and thus has become increasingly popular.

SUMMARY

In one or more embodiments, the present disclosure provides a wearable device. The wearable device includes a first element and a second element. The first element is configured to sense a bio-signal from a user. The second element is configured to transmit the bio-signal to a processor. The second element has a first surface and a second surface non-coplanar with the first surface. The first element is in contact with the first surface and the second surface of the second element.

In one or more embodiments, the present disclosure provides a wearable device. The wearable device includes a flexible conductive element and a conductive element. The flexible conductive element is configured to fit a user's skin The conductive element is embedded in the first flexible conductive element. The conductive element is configured to receive a signal from the conductive element.

In one or more embodiments, the present disclosure provides a wearable device. The wearable device includes an ear tip and a housing. The ear tip includes a flexible conductive element and a second conductive element. The conductive element is embedded in the flexible conductive element. The housing includes a first conductive pad. The first conductive pad is configured to receive a signal from the flexible conductive element through the conductive element.

BRIEF DESCRIPTION OF THE DRAWINGS

Aspects of the present disclosure are readily understood from the following detailed description when read with the accompanying figures. It should be noted that various features may not be drawn to scale. The dimensions of the various features may be arbitrarily increased or reduced for clarity of discussion.

Common reference numerals are used throughout the drawings and the detailed description to indicate the same or similar elements. The present disclosure will be more apparent from the following detailed description taken in conjunction with the accompanying drawings.

DETAILED DESCRIPTION

Figure 1:
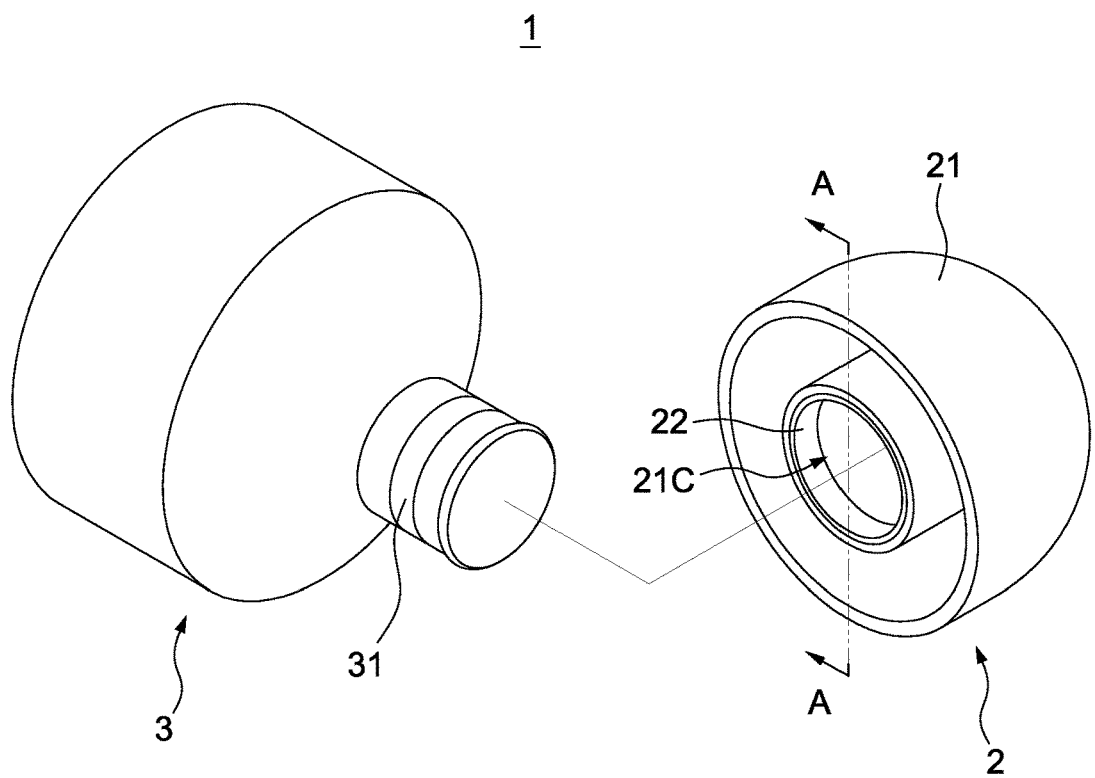
FIG. 1 illustrates a three-dimensional (3D) view of a wearable device in accordance with some embodiments of the present disclosure.

The following disclosure provides for many different embodiments, or examples, for implementing different features of the provided subject matter. Specific examples of components and arrangements are described below. These are, of course, merely examples and are not intended to be limiting. In the present disclosure, reference to the formation of a first feature over or on a second feature in the description that follows may include embodiments in which the first and second features are formed in direct contact, and may also include embodiments in which additional features may be formed between the first and second features, such that the first and second features may not be in direct contact. Besides, the present disclosure may repeat reference numerals and/or letters in the various examples. This repetition is for simplicity and clarity and does not in itself dictate a relationship between the various embodiments and/or configurations discussed.

Embodiments of the present disclosure are discussed in detail below. It should be appreciated, however, that the present disclosure provides many applicable concepts that can be embodied in a wide variety of specific contexts. The specific embodiments discussed are merely illustrative and do not limit the scope of the disclosure.

Referring to FIG. 1, it illustrates a 3D view of a wearable device 1 in accordance with some embodiments of the present disclosure. In some embodiments, the wearable device 1 may include an earpiece. The wearable device 1 includes an ear tip 2 and a housing 3 (or a body). The housing 3 may be fitted or received in the ear tip 2. In some embodiments, the housing 3 may be internal to the ear tip 2.

Figure 2:
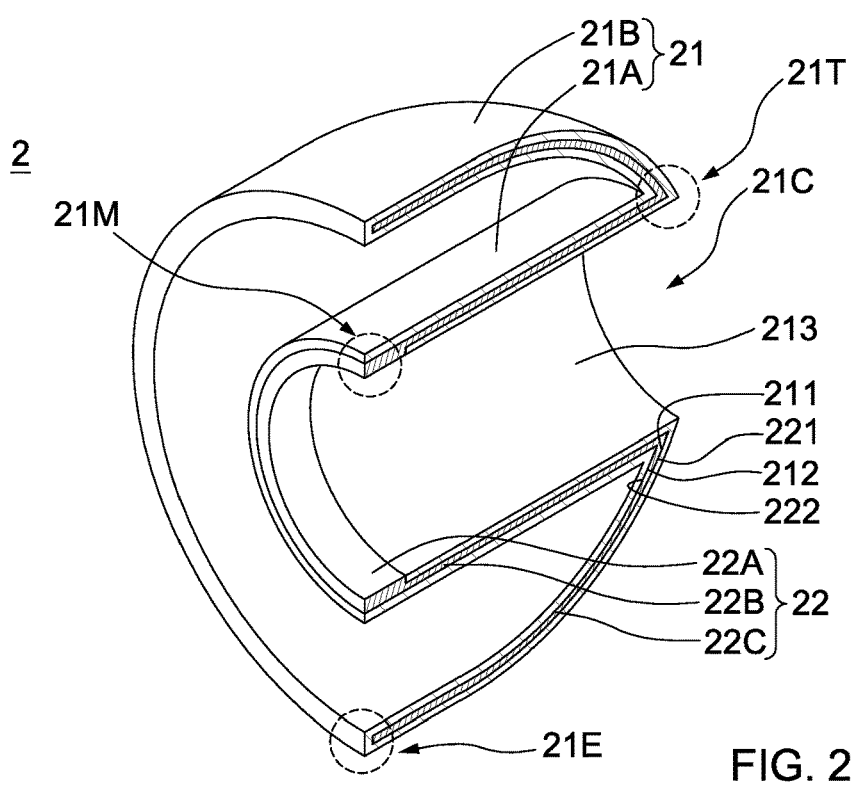
FIG. 2 illustrates a 3D sectional view of an ear tip along A-A line of FIG. 1.
Figure 3:
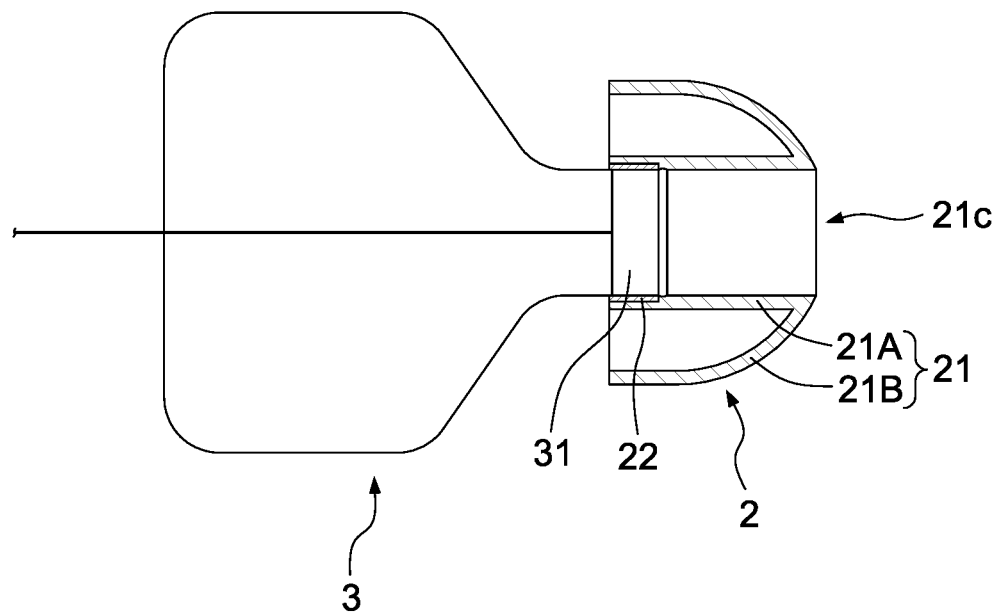
FIG. 3 illustrates a cross-sectional view of the wearable device of FIG. 1.

Referring to FIG. 2, it illustrates a 3D sectional view of the ear tip 2 along A-A line of FIG. 1. Referring to FIG. 3, it illustrates a cross-sectional view of the wearable device 1 of FIG. 1 when, for example, the housing 3 is received in the ear tip 2.

The application or usage of the ear tip 2 illustrated in the figures are for illustrative purpose only, and are not intended to limit the present disclosure. For example, the ear tip 2 of the present disclosure can be used in combination with any wearable device. In some embodiments, the ear tip 2 of the present disclosure can be used in combination with a piece of equipment that transmits audio signals. In some embodiments, the ear tip 2 of the present disclosure can be used in combination with a detecting device, an electronic device (such as a signal processing device) and/or another corresponding external device for further processing electrical signals collected through the ear tip 2. In some embodiments, the ear tip 2 of the present disclosure can be used as an ear plug, such as an ear plug for sleeping.

As shown in FIG. 1, FIG. 2, and FIG. 3, the ear tip 2 includes a first element 21 (e.g., a flexible conductive element) and a second element 22 (e.g., a second conductive element).

In some embodiments, from a cross-sectional view (such as the 3D cross-sectional view of FIG. 2), the first element 21 of the ear tip 2 includes a central portion 21A and a tail portion 21B extending from the central portion 21A. In some embodiments, the form of the conductive layer 21 may be customized to fit in a user's ear canal. In some embodiments, from a 3D view (such as the 3D view of FIG. 1), the first element 21 may include, for example, a basically hemispherical and/or hemi-ellipsoidal form.

As shown in FIG. 2, the central portion 21A of the first element 21 has a top 21T and a bottom 21M opposite the top 21T. When the wearable device 1 is worn by a user, the top 21T of the ear tip 2 sits more deeply into the ear canal than does the bottom 21M. The central portion 21A has an inner surface 213 defining a through hole 21C from the bottom 21M to the top 21T. As such, the sound can be transmitted via the through hole 21C. In some embodiments, while the wearable device 1 is worn by a user, the top 21T may be closer to the user's canal or may be deeper in the user's canal than the bottom 21M to facilitate the detection of the variation of skin charge. In some embodiments, the top 21T is closer than the bottom 21M to a blood vessel (such as the internal carotid artery or the internal jugular vein) of the user. The bottom 21M may be adapted or shaped to receive the housing 3 of the wearable device 1. In some embodiments, a buckle portion 3T of the housing 3 and/or the bottom 21m may be used as a position confinement element when fitting the housing 3 in the ear tip 2.

As shown in FIG. 2, the second element 22 is embedded in the first element 21. In some embodiments, the second element 22 may be partially covered by the first element 21. The first element 21 may be in contact with the second element 22. In some embodiments, a shape of the second element 22 may be conformal to a shape of the first element 21. The second element 22 may extend from an end (e.g., the bottom 21M) of the central portion 21A of the first element 21 to an end 21E of the tail portion 21B of the first element 21. In some embodiments, the first element 21 may be a sensing element, e.g., an electrode. In some embodiments, the second element 22 may include an electrode. The second element 22 may be electrically coupled with a temperature sensor (e.g., a thermistor), or a capacitive sensor of the housing 3.

The second element 22 may have a first surface 221 and a second surface 222 non-coplanar with the first surface 221. The first surface 221 may be opposite the second surface 222. The first element 21 may have a first surface 211 and a second surface 212 non-coplanar with the first surface 211. The first surface 211 may be opposite the second surface 212. The first surface 211 of the first element 21 may be in contact with the first surface 221 of the second element 22. The second surface 212 of the first element 21 may be in contact with the second surface 222 of the second element 22.

Still referring to FIG. 2, the second element 22 may include a first portion 22A (e.g., a conductive pad), a second portion 22B (e.g., a conductive foil), and a third portion 22C (e.g., a conductive foil). The first portion 22A and the second portion 22B may be connected with each other. The second portion 22B may extend from the first element 21 to the first portion 22A. The second portion 22B and the third portion 22C may be connected with each other. The first portion 22A may be exposed from the inner surface 213 of the central portion 21A of the first element 21. The first portion 22A may protrude from the inner surface 213. The first portion 22A may have a thickness along a radial direction greater than that of the second portion 22B and the third portion 22C. The first portion 22A may be surrounded by the central portion 21A of the first element 21. The first portion 22A may have an annular shape. The second portion 22B may be embedded in the central portion 21A of the first element 21. The third portion 22C may be embedded in the tail portion 21B of the first element 21. The third portion 22C may have an end away from the second portion 22B and covered by the end 21E of the tail portion 21B of the first element 21. In other words, the end of the third portion 22C may not be exposed from the first element 21.

In some embodiments, the first element 21 may include a conductive layer. In some embodiments, the material of the first element 21 may include a flexible conductive material, for example, a conductive silicone, a thermal conductive silicone, a conductive rubber, a conductive sponge, a conductive fabric, or a conductive fiber. The first element 21 may be configured to fit a user's skin or user's canal. The first element 21 may be soft and flexible enough for the user to wear for an extended time period without feeling uncomfortable. In some embodiments, a material of the second element 22 may include a conductive material such as a metal or metal alloy. Examples include gold (Au), silver (Ag), aluminum (Al), copper (Cu), or an alloy thereof. In some embodiments, a conductivity of the first element 21 may be different from that of the second element 22. In some embodiments, the conductivity of the second element 22 may be greater than that of the first element 21. In some embodiments, a resistivity of the first element 21 may be different from that of the second element 22.

The first element 21 may be configured to sense a bio-signal from a user. The first element 21 may be configured to collect one or more bio-signals associated with the user of the earpiece. In some embodiments, the first element 21 may be configured to obtain electrical signals which represent the bio-signals of the user. The first element 21 may be electrically coupled with the second element 22 embedded therein. The first element 22 may be configured to receive a signal from the first element 21. The second element may be configured to transmit the bio-signal to a processor in the housing 3 (not shown). While being worn by a user, the first element 21 is closer than the second element 22 to an internal carotid artery or an internal jugular vein of the user. The electrical signals collected by the first element 21 may be transmitted to the embedded second element 22, which provides a low-resistance/high-conductance transmission path for the electrical signals. Furthermore, the second portion 22B and the third portion 22C of the second element 22 extend into the first element 21. This arrangement enlarges the contact area between the second element 22 and the first element 21. As such, the total resistance of the ear tip 2 can be relatively low and thus the quality of the electrical signals can be improved.

As shown in FIG. 1 and FIG. 3, the housing 3 may include a conductive pad 31. The conductive pad 31 may be arranged at a location and/or with a shape corresponding to the first portion 22A (e.g., the conductive pad) of the second element 22. For example, the conductive pad 22A and the conductive pad 31 may be in contact with each other while the housing 3 is received in the ear tip 2 as shown in FIG. 3. The electrical signals collected via the first element 21 may be transmitted to an electronic device (not shown in the figures) in the housing 3 through the second element 22 and the conductive pad 31. Then, the electrical signals may be transmitted to an outer apparatus or device for being further processed.

In some embodiments, the bio-signals may include one or more of a pulse travel time (PTT), an electroencephalogram (EEG), electrocardiogram (ECG), electromyogram (EMG), electrooculogram (EOG), galvanic skin response (GSR), sweat composition, pH, or other biologically-relevant information associated with the user of the earpiece. For example, the electrical signals collected by the first element 21 may be used to produce an ECG from a user. In some embodiments, the conductive layer 21 may include a thermal conductive material and the heat can be transmitted from the user (or user's ear canal) to a temperature sensor (e.g., a thermistor) of the housing 3 through the conductive element 22 and the conductive layer 21. In other words, the user's temperature may be detected by the temperature sensor of the housing 3.

In some comparative embodiments, a wearable device may be used for collecting the bio-signals associated with a user. The wearable device may include an ear tip, which may include a dielectric main body and one or more metal pads disposed on an outer surface of the dielectric main body. The metal pads may be used to collect the bio-signals from the user and thus may be in contact with the user's skin when the ear tip is set in the user's ear canal. However, the material of the metal pads and the unsmooth topography caused by the metal pads may detract from the user's wearing experience. For example, the metal material of the metal pads on the outer surface of the ear tip may cause an uncomfortable feeling or an allergic reaction. In our present disclosure, the second element 22 is embedded in the flexible first element 21. As such, the second element 22 is physically separated from the user's skin when the wearable device 1 is worn by the user. It is of benefit to improve the user's wearing experience since the soft and flexible material of the flexible first element 21 is suitable for a long-term wearing behavior. Hence, the wearable device 1 as disclosed in the present disclosure can be used for collecting the bio-signals (or electrical signals representing the bio-signals) and providing a comfortable wearing experience for users.

Figure 4:
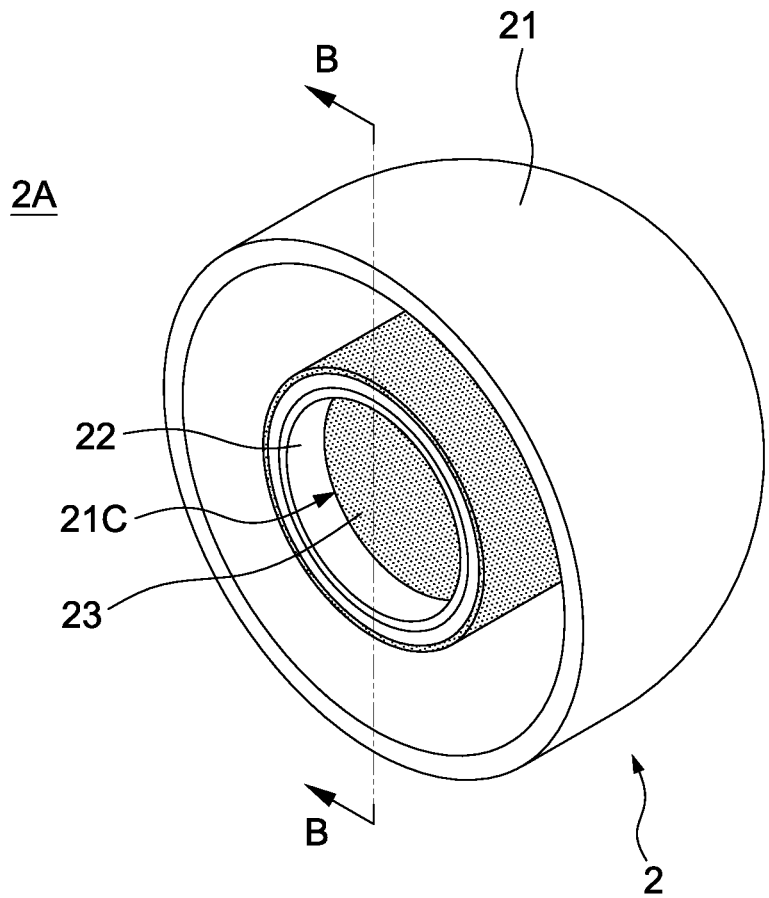
FIG. 4 illustrates a 3D view of an ear tip in accordance with some embodiments of the present disclosure.
Figure 5:
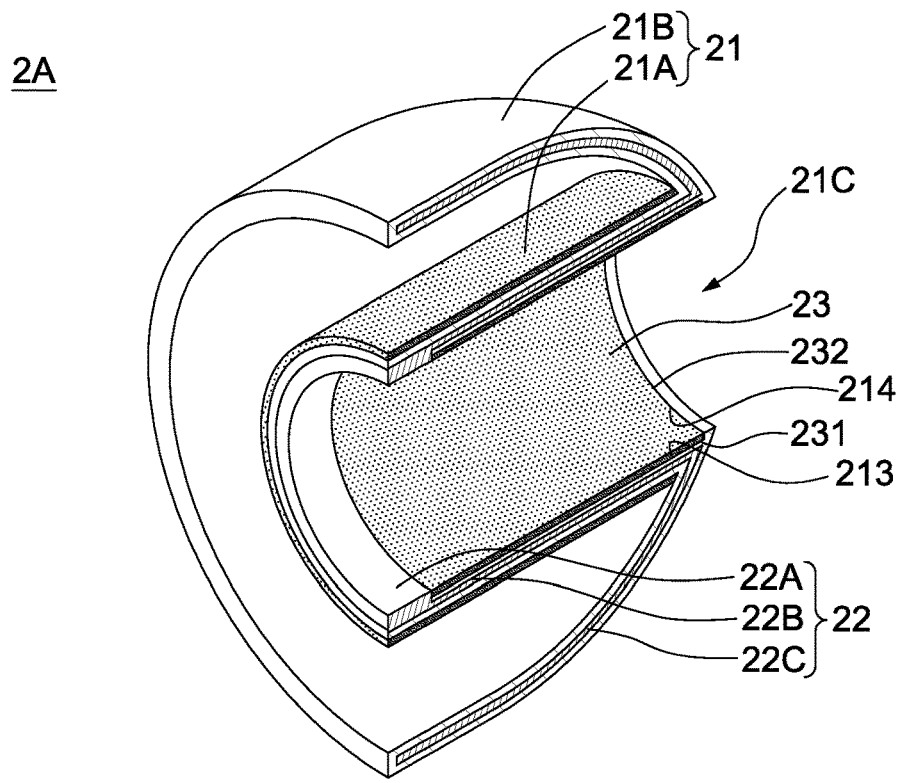
FIG. 5 illustrates a 3D sectional view of an ear tip along B-B line of FIG. 4.

Referring to FIG. 4, FIG. 4 illustrates a 3D view of an ear tip 2A in accordance with some embodiments of the present disclosure. Referring to FIG. 5, FIG. 5 illustrates a 3D sectional view of the ear tip 2A along B-B line of FIG. 4. The ear tip 2A of FIG. 4 and FIG. 5 is similar to the ear tip 2 of FIG. 1 and FIG. 2, and the differences therebetween are described below.

The ear tip 2A further includes an insulation element 23 (or an insulation layer) surrounding the central portion 21A of the conductive layer 21. The insulation element 23 may be in contact with the inner surface 213 of the first element 21. The insulation element 23 may have a first surface 231 and a second surface 232. The first element 21 may have a surface 214 connected with the inner surface 213 of the first element 21. The inner surface 213 of the first element 21 may be in contact with the first surface 231 of the insulation element 23. The surface 214 of the first element 21 may be in contact with the second surface 232 of the insulation element 23.

In some embodiments, the insulation element 23 may include a dielectric material. In some embodiments, the insulation element 23 may include, for example, rubber, silicon, sponge, or other suitable material such as an elastic material, a soft material, or a flexible material. The insulation element 23 may be soft and flexible enough for the user to wear for an extended time period without feeling uncomfortable.

Figure 6:
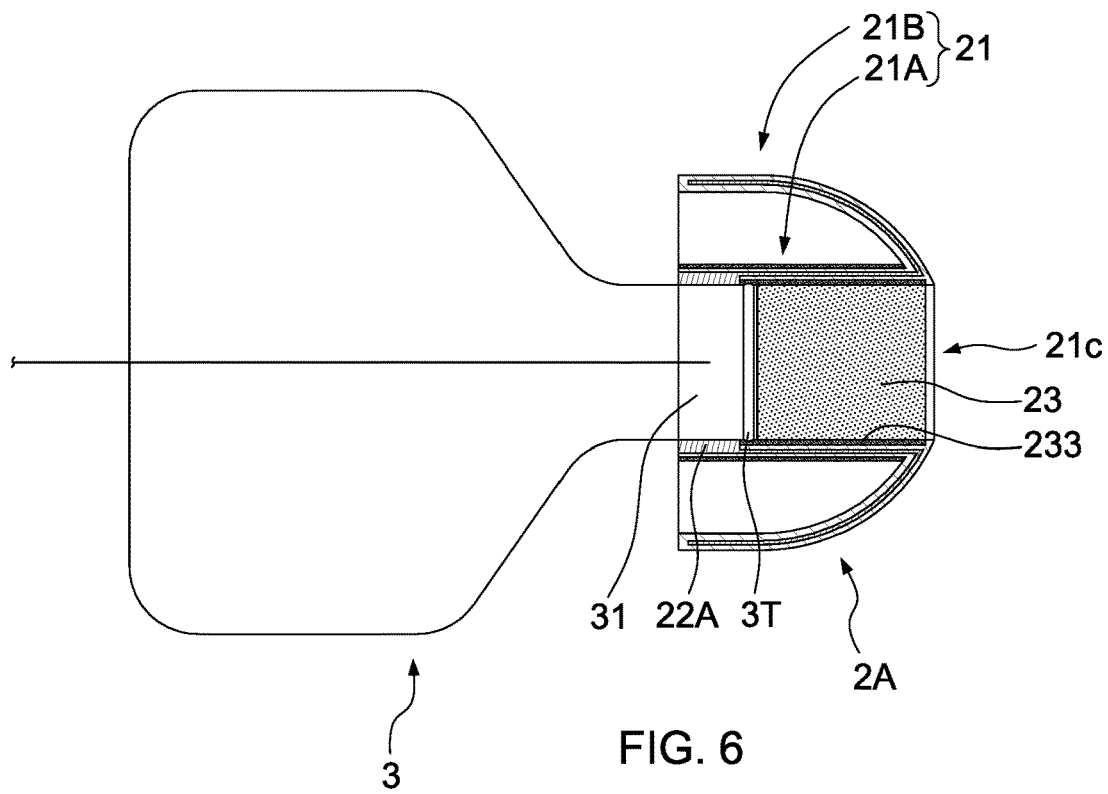
FIG. 6 illustrates a cross-sectional view of the wearable device in accordance with some embodiments of the present disclosure.

Referring to FIG. 6, FIG. 6 illustrates a cross-sectional view of a wearable device 1A in accordance with some embodiments of the present disclosure. In some embodiments, the wearable device 1A may include an earpiece. The wearable device 1A of FIG. 6 is similar to the wearable device 1 of FIG. 3, and the differences therebetween are described below.

The wearable device 1A of FIG. 6 includes the ear tip 2A as illustrated in FIG. 5 and the housing 3 as illustrated in FIG. 3. The first portion 22A of the second element 22 is exposed from an inner surface 233 of the insulation element 23. The first portion 22A is exposed and in contact with the conductive pad 31. The insulation element 23 is disposed between the first element 21 and the outer surface of the housing 3. The insulation element 23 may be in contact with the buckle portion 3T of the housing 3. As such, the first element 21 is physically separated from the housing 3 by the insulation element 23. The electrical signals collected by the first element 21 would be received by the housing 3 only through the conductive pad 31, rather than another portion (e.g., the buckle portion 3T) of the housing 3. This may reduce the noise that occurs when the first element 21 and the buckle portion 3T of the housing 3 are in contact with each other.

Figure 7:
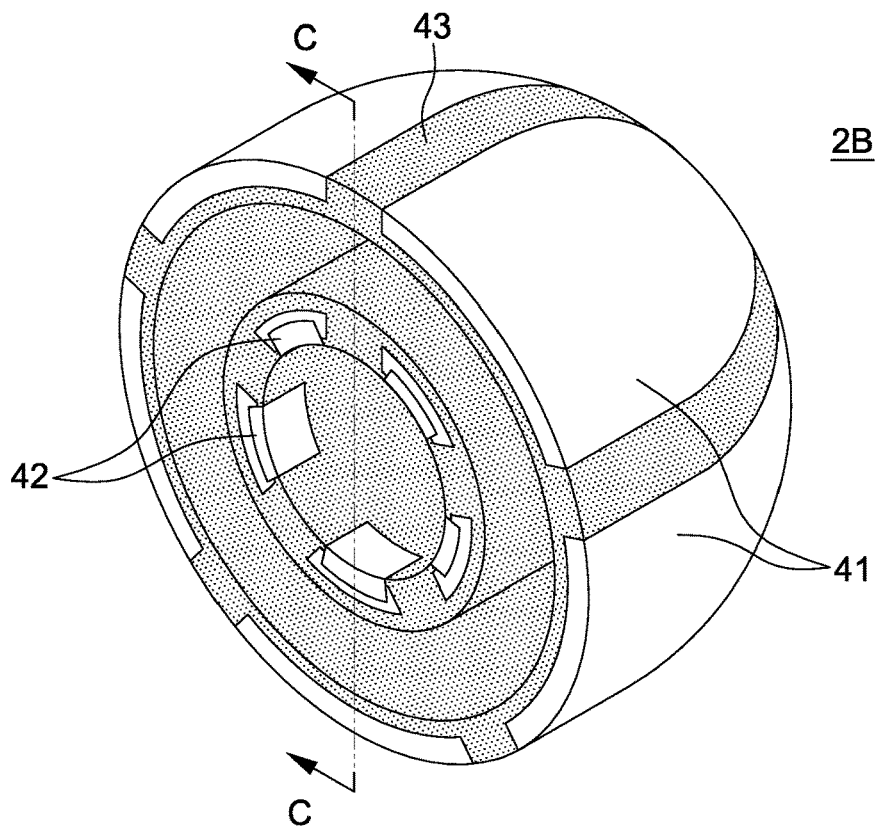
FIG. 7 illustrates a 3D view of an ear tip in accordance with some embodiments of the present disclosure.
Figure 8:
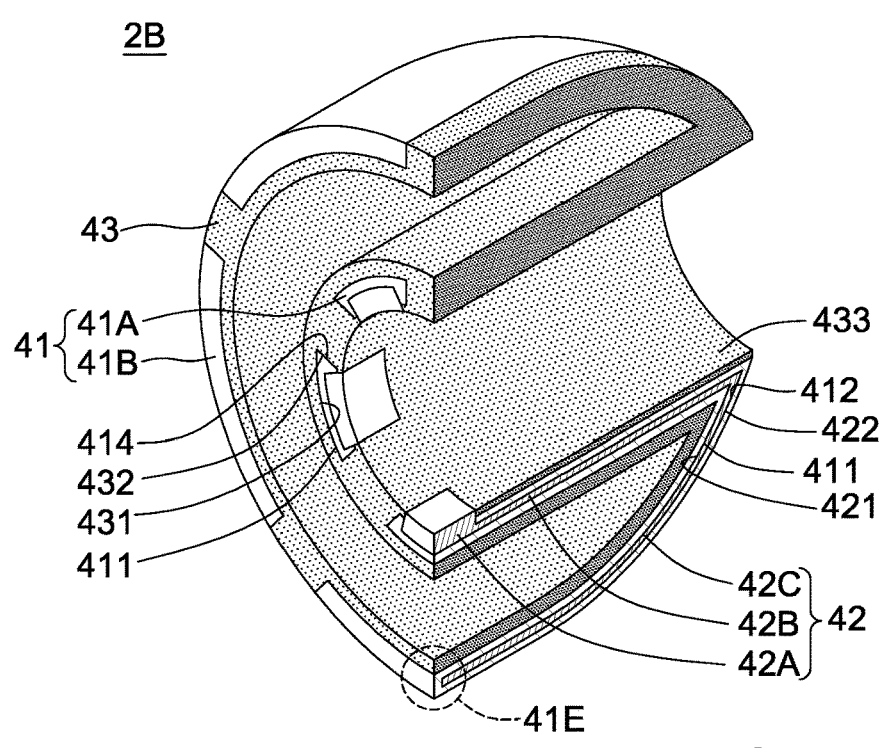
FIG. 8 illustrates a 3D sectional view of an ear tip along C-C line of FIG. 7.
Figure 9:
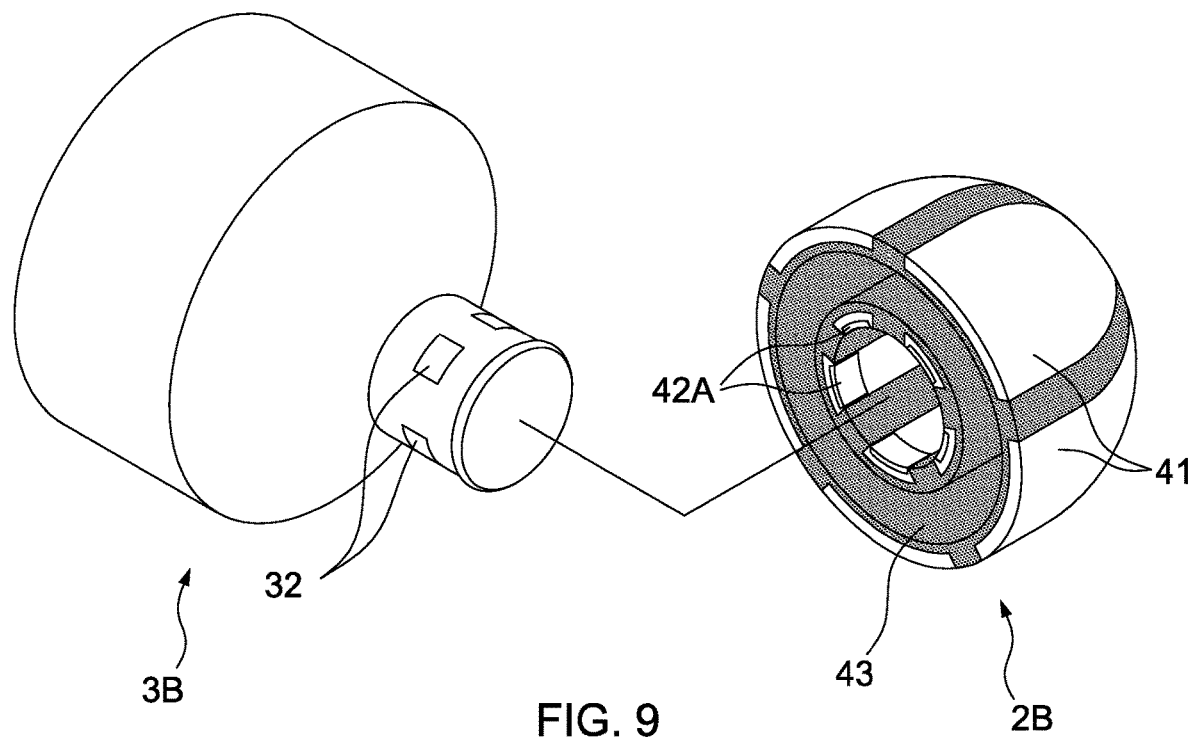
FIG. 9 illustrates a 3D view of a wearable device in accordance with some embodiments of the present disclosure.

Referring to FIG. 7, it illustrates a 3D view of an ear tip 2B in accordance with some embodiments of the present disclosure. Referring to FIG. 8, it illustrates a 3D sectional view of the ear tip 2B along C-C line of FIG. 7. Referring to FIG. 9, it illustrates a 3D view of a wearable device 1B in accordance with some embodiments of the present disclosure. In some embodiments, the wearable device 1B may include an earpiece. As shown in FIG. 9, the wearable device 1B includes the ear tip 2B of FIG. 7 and a housing 3B. The housing 3B may be fitted or received in the ear tip 2B. In some embodiments, the housing 3B may be internal to the ear tip 2B.

The ear tip 2B includes a plurality of first elements 41 (e.g., a plurality of flexible conductive elements), a plurality of second elements 42 (e.g., a plurality of conductive elements), and an insulation element 43. The plurality of first elements 41 may include a material similar to the first element 21. The plurality of second elements 42 may include a material similar to the second element 22. The insulation element 43 may include a material similar to the insulation element 23.

In some embodiments, from a cross-sectional view (such as the 3D cross-sectional view of FIG. 8), the first elements 41 of the ear tip 2B each includes a central portion 41A and a tail portion 41B extending from the central portion 41A. In some embodiments, from a 3D view (such as the 3D view of FIG. 7), the central portion 41A of the first elements 41 may include, for example, a basically striped form, and the tail portion 41B of the first elements 41 may include, for example, a basically sector form.

As shown in FIG. 8, each of the plurality of second elements 42 is embedded in one of the first elements 41. Each of the second elements 42 may be partially covered by one of the first elements 41. Each of the second element 22 may be in contact with one of the first elements 41. In some embodiments, a shape of the second elements 42 may be conformal to a shape of the first elements 41.

The plurality of second elements 42 each has a first surface 421 and a second surface 422 non-coplanar with the first surface 421 thereof. The first surface 421 may be opposite the second surface 422. The plurality of first elements 41 each has a first surface 411 and a second surface 412 non-coplanar with the first surface 411 thereof. The first surface 411 may be opposite the second surface 412. The first surface 411 of each of the first elements 41 may be in contact with the first surface 421 of one of the second elements 42, respectively, and the second surface 412 of each of the first elements 41 may be in contact with the second surface 42 of one of the second elements 42, respectively.

Still referring to FIG. 8, the second elements 42 may each include a first portion 42A (e.g., a conductive pad), a second portion 42B (e.g., a conductive foil), and a third portion 42C (e.g., a conductive foil). The first portion 42A and the second portion 42B may be connected with each other. The second portion 42B may be extended from one of the first elements 41 to the first portion 42A. The second portion 42B and the third portion 42C may be connected with each other. The first portion 42A may be exposed from an inner surface 433 of the insulation element 43 first elements 41. The first portion 42A may protrude from the inner surface 433 of the insulation element 43. The first portion 42A may have a thickness along a radial direction greater than that of the second portion 42B and the third portion 42C. The first portion 42A may have a curved shape. The second portion 42B may be embedded in the central portion 41A of the conductive layer 41. The third portion 42C may be embedded in the tail portion 41B of the first elements 41. The third portion 42C may have an end away from the second portion 42B and covered by an end 41E of the tail portion 41B of the first elements 41. In other words, the end of the third portion 42C may not be exposed from the first elements 41.

As shown in FIG. 7, the insulation element 43 may surround the first elements 41. The insulation element 43 has a first surface 431 and a second surface 432 non-coplanar with the first surface 431. The first surface 431 may be connected to the second surface 432. The first elements 41 each have a surface 414 non-coplanar with the first surface 411 or the inner surface 413. The surface 414 may extend between the first surface 411 and the inner surface 413. The first surface 411 of the first elements 41 may be in contact with the first surface 431 of the insulation element 43. The surface 414 of the first elements 41 may be in contact with the second surface 432 of the insulation element 43.

In some embodiments, the insulation element 43 may be disposed between two of the first elements 41. The first elements 41 may be spaced apart from each other by the insulation element 43. Owing to the existence of the insulation element 43, the first elements 41 may be electrically isolated from each other. As such, each of the first elements 41 may collect one or more electrical signals (representing bio-signals) of the user without interference from other electrical signals collected via other of the first elements 41.

Different elements of the first elements 41 may be used to collect different bio-signals associated with the user of the earpiece. In some embodiments, the first elements 41 may be used to obtain different electrical signals which represent different bio-signals of the user. For example, the bio-signals may include one or more of a pulse travel time (PTT), an electroencephalogram (EEG), electrocardiogram (ECG), electromyogram (EMG), electrooculogram (EOG), galvanic skin response (GSR), sweat composition, pH, or other biologically-relevant information associated with the user of the earpiece. Furthermore, the first elements 41 may collect a reference voltage for cancelling noise. In other words, one of the first elements 41 may be used as a voltage right leg drive (VRLD).

Each of the first elements 41 may be electrically coupled with one of the second elements 42 embedded therein. The electrical signals collected by the first elements 41 may be transmitted to the embedded second elements 42, which provides a low-resistance/high-conductance transmission path for the electrical signals. Furthermore, the second portion 42B and the third portion 42C of the second elements 42 extend into the first elements 41. This arrangement enlarges the contact area between the second elements 42 and the first elements 41. As such, the total resistance of the ear tip 2B can be relatively low and thus the quality of the electrical signals can be improved.

The positions and the numbers of the conductive layers and the conductive elements in the ear tip 2B illustrated in the figures are for illustrative purpose only, and are not intended to limit the present disclosure. For example, there may be any number of first elements and second elements in the ear tip 2B based on design requirements. For example, conductive layers and conductive elements in the ear tip 2B may be arranged in any position based on design requirements.

Referring to FIG. 9, the housing 3B includes a plurality of conductive pads 32. The conductive pads 32 may be arranged at a location and/or with a shape corresponding to the first portions 42A (e.g., the conductive pad) of the second elements 42. For example, the conductive pads 42A and the conductive pads 32 may be in contact with each other while the housing 3B is received in the ear tip 2B. The electrical signals collected via the first elements 41 may be transmitted to an electronic device (not shown in the figures) in the housing 3B through the second elements 42 and the conductive pads 32. Then, the electrical signals may be transmitted to an outer apparatus or device for being further processed. By electrically coupling a first elements 41 plurality of first elements 41 with the conductive pads 32 through the second elements 42, a plurality of bio-signals can be collected by the wearable device 1B when it is worn by a user.

Figure 10:
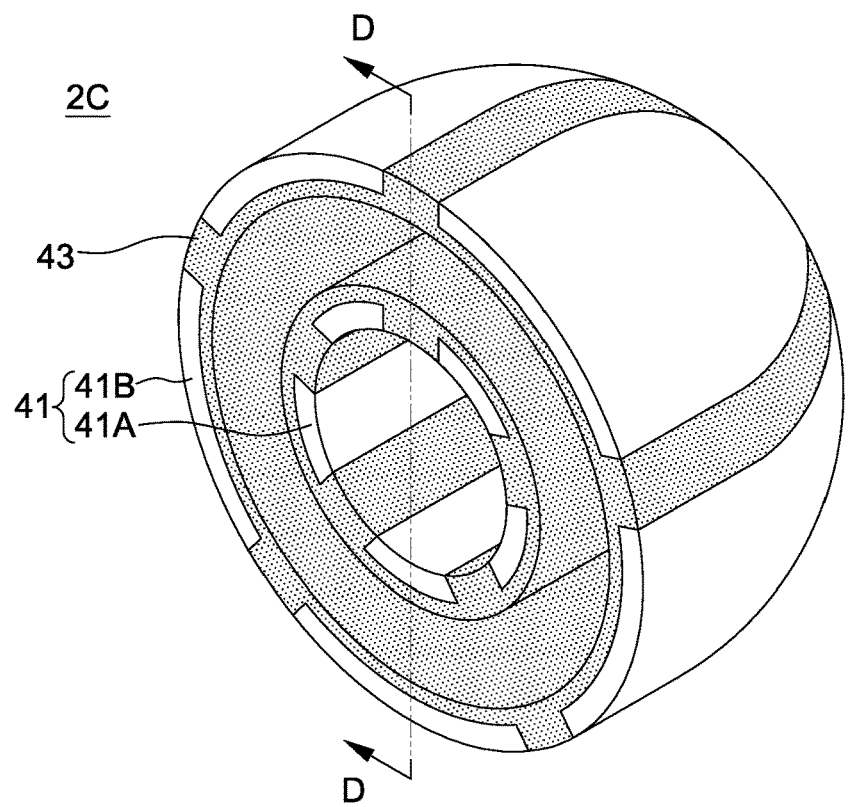
FIG. 10 illustrates a 3D view of an ear tip in accordance with some embodiments of the present disclosure.
Figure 11:
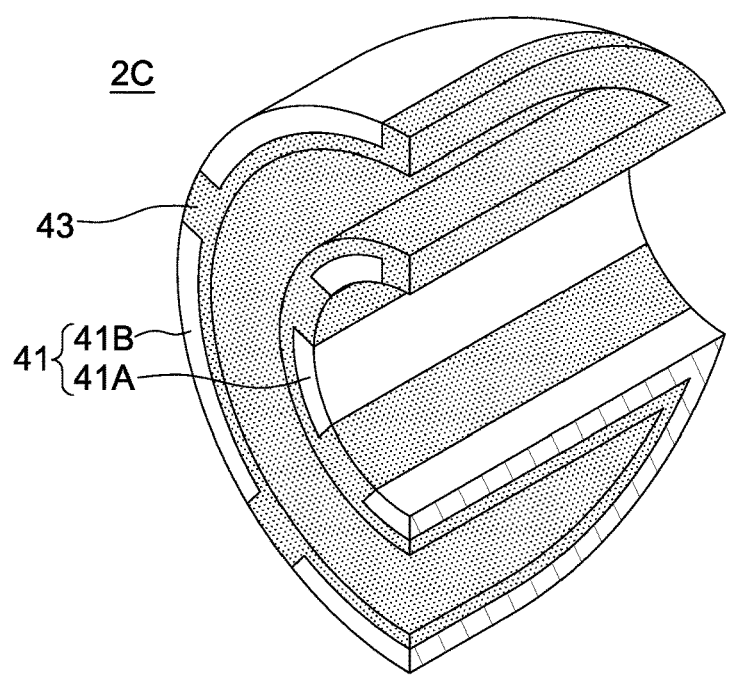
FIG. 11 illustrates a 3D sectional view of an ear tip along D-D line of FIG. 10.

Referring to FIG. 10, it illustrates a 3D view of an ear tip 2C in accordance with some embodiments of the present disclosure. Referring to FIG. 11, it illustrates a 3D sectional view of the ear tip 2C along D-D line of FIG. 10. A wearable device may include the ear tip 2C and a housing received in the ear tip 2C. The ear tip 2C of FIG. 10 is similar to the ear tip 2B of FIG. 7, and the differences therebetween are described below.

The ear tip 2C of FIG. 10 excludes an element (e.g., the second element 42 of the ear tip 2B in FIG. 9) embedded in the first elements 41. An end of the central portion 41A of the conductive layer 41 may be in contact with one of conductive pads of a housing (e.g., the conductive pads 32 of the housing 3B in FIG. 9). The electrical signals collected via the first elements 41 may be directly transmitted to a housing (e.g., the housing 3B of FIG. 9). The cost of the ear tip 2C can be relatively low by excluding the embedded element (e.g., the conductive element 42 of the ear tip 2B in FIG. 9). By adjusting the conductivity of the first elements 41 of the ear tip 2C, the quality of the electrical signals transmitted in the ear tip 2C may still be retained at an acceptable level.

Figure 12:
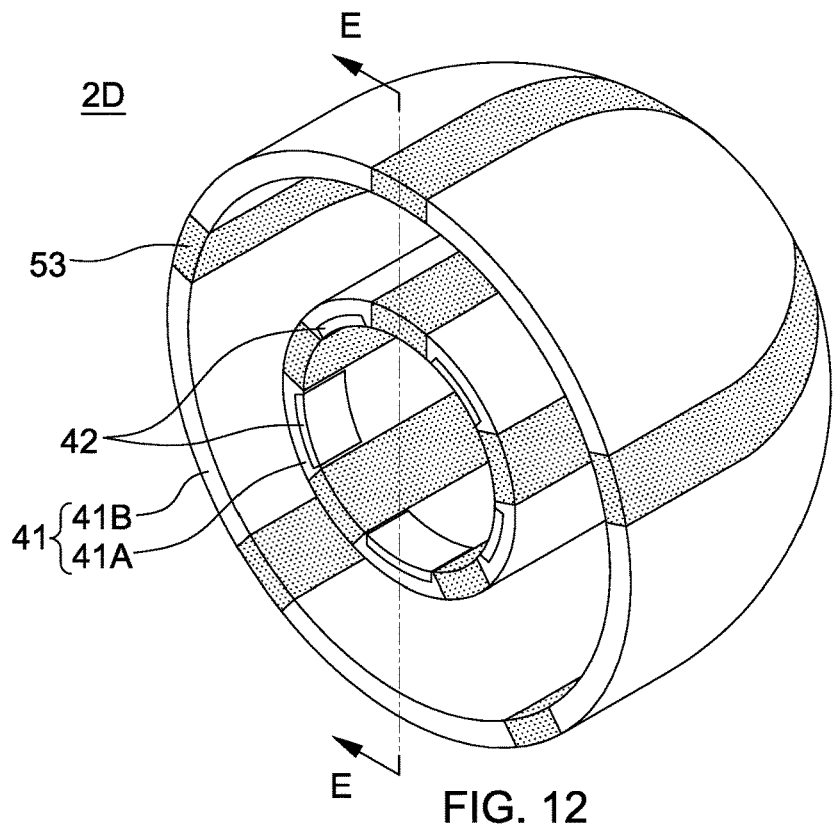
FIG. 12 illustrates a 3D view of an ear tip in accordance with some embodiments of the present disclosure.
Figure 13:
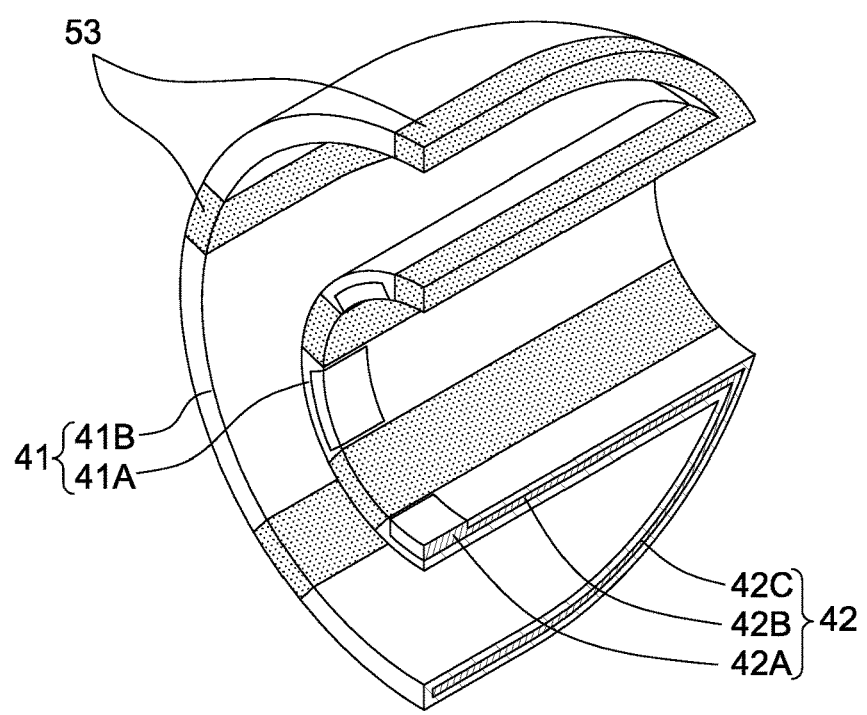
FIG. 13 illustrates a 3D sectional view of an ear tip along E-E line of FIG. 14.

Referring to FIG. 12, it illustrates a 3D view of an ear tip 2D in accordance with some embodiments of the present disclosure. Referring to FIG. 13, it illustrates a 3D sectional view of the ear tip 2D along E-E line of FIG. 12. A wearable device may include the ear tip 2D and a housing received in the ear tip 2D. The ear tip 2D of FIG. 12 is similar to the ear tip 2B of FIG. 7, and the differences therebetween are described below.

As shown in FIG. 12, the ear tip 2D includes a plurality of insulation elements 53 interleaved with the conductor layers 41. The insulation elements 53 may include a material similar to the insulation element 23. The first elements 41 may be spaced apart from each other by the insulation elements 53. In some embodiments, owing to the existence of the insulation elements 53, the first elements 41 may be electrically isolated from each other. As such, each of the first elements 41 may collect one or more electrical signals (representing bio-signals) from the user without interference from other electrical signals collected via other layers of the first elements 41.

Figure 14:
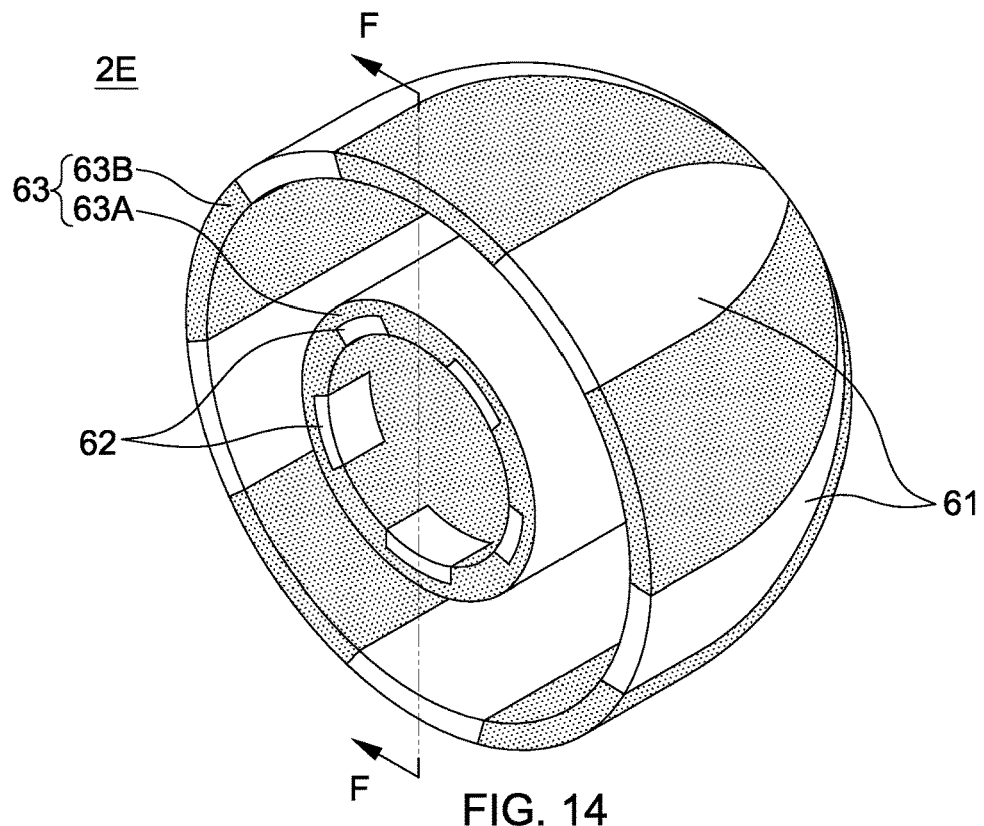
FIG. 14 illustrates a 3D view of an ear tip in accordance with some embodiments of the present disclosure.
Figure 15:
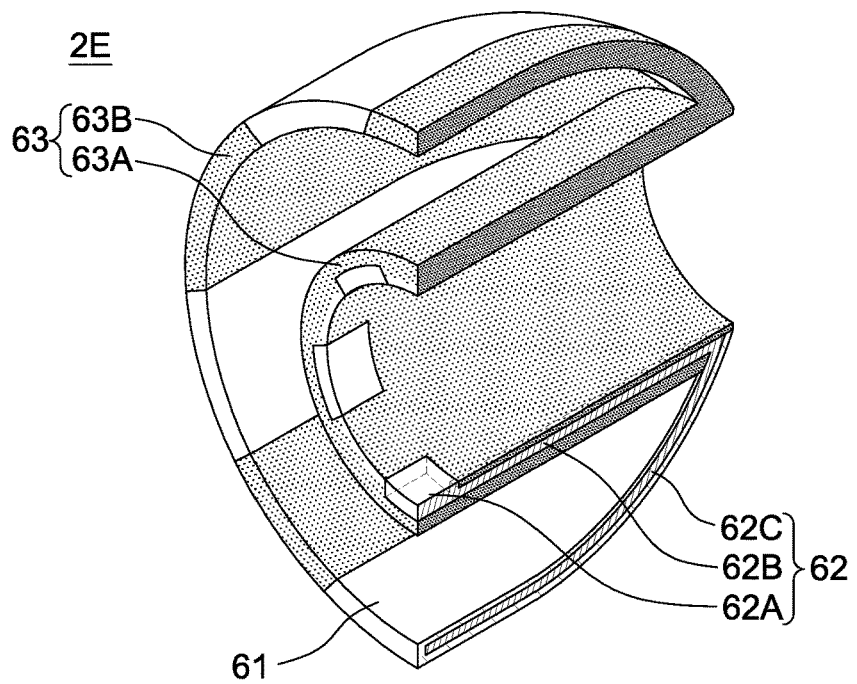
FIG. 15 illustrates a 3D sectional view of an ear tip along F-F line of FIG. 14.
Figure 16:
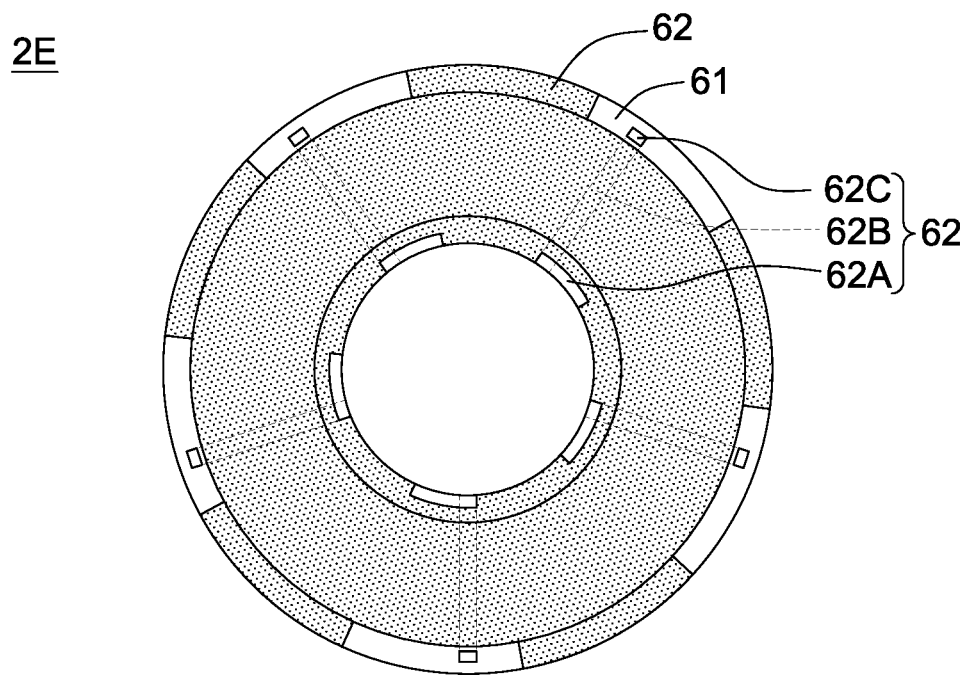
FIG. 16 illustrates a top view of the ear tip of FIG. 14.

Referring to FIG. 14, FIG. 14 illustrates a 3D view of an ear tip 2E in accordance with some embodiments of the present disclosure. Referring to FIG. 15, it illustrates a 3D sectional view of the ear tip 2E along F-F line of FIG. 14. Referring to FIG. 16, it illustrates a top view of the ear tip 2E of FIG. 14. A wearable device may include the ear tip 2E and a housing received in the ear tip 2E. The ear tip includes a plurality of first elements 61, a plurality of second elements 62, and an insulation element 63. The plurality of first elements 61 may include a material similar to the first element 21. The plurality of second elements 62 may include a material similar to the second element 22. The insulation element 63 may include a material similar to the insulation element 23.

As shown in FIG. 15, the insulation element 63 includes a central portion 63A and a tail portion 63B connected to the central portion 63A. The second elements 62 may each include a first portion 62A (e.g., a conductive pad), a second portion 62B (e.g., a conductive foil), and a third portion 62C (e.g., a conductive foil). The second portion 62B may extend into the insulation element 63 to the first portion 62A. The first portion 62A and the second portion 62B may be surrounded by the central portion 63A of the insulation element 63. In some embodiments, the first portion 62A and the second portion 62B may be embedded in the central portion 63A of the insulation element 63. The first portion 62A may have a surface exposed from the central portion 63A of the insulation element 63. The second portion 62B may be covered by the central portion 63A of the insulation element 63. As shown in FIG. 16, the first portion 62A and the second portion 62B may form an L shape. A width of the first portion 62A may be greater than that of the second portion 62B. The third portion 62C may be surrounded by one of the first elements 61. The third portion 62C may be embedded in one of the first elements 61. The central portion 63A of the insulation element 63 and one of the first elements 63 may form an interface, where the portion 62B and the third portion 62C of one of the second elements 62 are connected.

Each of the conductive layers 63 may be spaced apart by the tail portion 63B of the insulation element 63. Owing to the existence of the insulation element 63, the first elements 61 may be electrically isolated from each other. As such, each of the first elements 61 may collect one or more electrical signals (representing bio-signals) from the user without interference from other electrical signals collected via other layers of the first elements 61.

Different elements of the first elements 61 may be used to collect different bio-signals associated with the user of the earpiece. In some embodiments, the first elements 61 may be used to obtain different electrical signals which represent different bio-signals of the user. The category of the bio-signals is discussed the previous paragraphs and is not repeated here. Each of the first elements 61 may be electrically coupled with one of the second elements 62 embedded therein. The electrical signals collected by the first elements 61 may be transmitted to the embedded second elements 62, which provides a low-resistance/high-conductance transmission path for the electrical signals. The electrical signals collected via the first elements 61 may be transmitted to a housing (e.g., the housing 3B of FIG. 9) through the embedded second elements 62.

The positions and numbers of the conductive layers and conductive elements in the ear tip 2E illustrated in the figures are for illustrative purpose only, and are not intended to limit the present disclosure. For example, there may be any number of first elements and second elements in the ear tip 2E based on design requirements. For example, conductive layers and conductive elements in the ear tip 2E may be arranged in any position based on design requirements.

Figure 17:
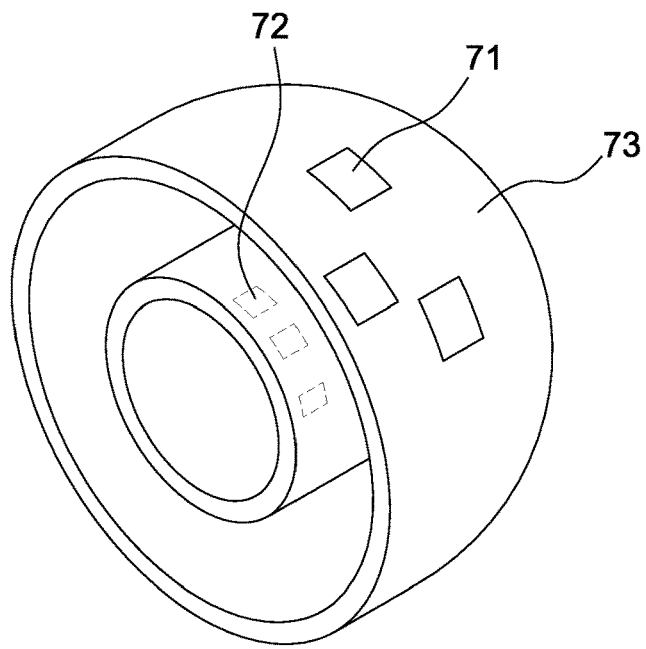
FIG. 17 illustrates a 3D view of an ear tip in accordance with some embodiments of the present disclosure.
Figure 17A:
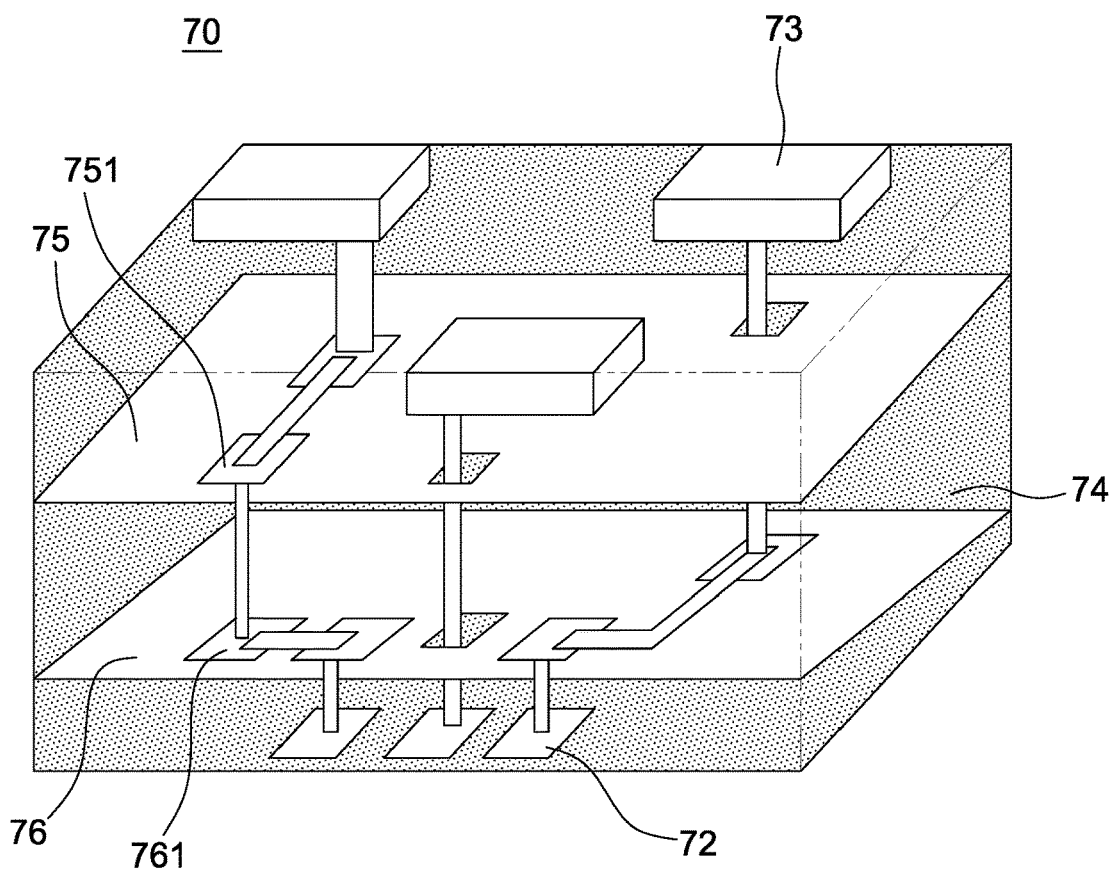
FIG. 17A illustrates a 3D illustrative diagram of a redistribution structure in the ear tip of FIG. 17.

Referring to FIG. 17, FIG. 17 illustrates a 3D view of an ear tip 2F in accordance with some embodiments of the present disclosure. Referring to FIG. 17, FIG. 17A illustrates a 3D illustrative diagram of a redistribution structure 70 in the ear tip 2F of FIG. 17. A wearable device may include the ear tip 2F and a housing received in the ear tip 2F.

As shown in FIG. 17, the ear tip includes a plurality of flexible conductive elements 71, a plurality of conductive elements 72, and an insulation element 73. The plurality of flexible conductive elements 71 may include a material similar to the first element 21. The plurality of conductive elements 72 may include a material similar to the second element 22. The insulation element 73 may include a material similar to the insulation element 23.

The flexible conductive elements 71 may include conductive pads. The flexible conductive elements 71 may be surrounded by the insulation element 73. The flexible conductive elements 71 may be spaced apart from each other by the insulation element 73. The conductive elements 72 may include conductive pads. The conductive elements 72 may be surrounded by the insulation element 73. The conductive elements 72 may be spaced apart from each other by the insulation element 73. Each of the flexible conductive elements 71 may be electrically coupled with the conductive elements 72 through the redistribution structure as shown in FIG. 17A. The redistribution structure 70 includes a dielectric layer 75, a plurality of conductive traces 751 disposed on the dielectric layer 75, a dielectric layer 76, and a plurality of conductive traces 761 disposed on the dielectric layer 76. The dielectric layer 75 and the dielectric layer 76 are disposed in the insulation element 73 and between the flexible conductive elements 71 and the conductive elements 72. The dielectric layer 75 is disposed over the dielectric layer 76. Each of the flexible conductive elements 71 may be electrically coupled with one of the conductive elements 72 through the conductive traces 751 and the conductive traces 761, respectively.

Different layers of the flexible conductive elements 71 may be used to collect different bio-signals associated with the user of the earpiece. In some embodiments, the flexible conductive elements 71 may be used to obtain different electrical signals which represent different bio-signals of the user. The category of the bio-signals is discussed the previous paragraphs and is not repeated here. The electrical signals collected by the flexible conductive elements 71 may be transmitted to the conductive elements 72 through the redistribution structure 70. The electrical signals collected via the flexible conductive elements 71 may be transmitted to a housing (e.g., the housing 3B of FIG. 9) through the embedded conductive elements 72.

The positions and the numbers of the conductive layers and the conductive elements in the ear tip 2F illustrated in the figures are for illustrative purpose only, and are not intended to limit the present disclosure. For example, there may be any number of first elements and second elements in the ear tip 2F based on design requirements. For example, conductive layers and conductive elements in the ear tip 2F may be arranged in any position based on design requirements.

Although the wearable device illustrated in FIG. 1, FIG. 3, FIG. 6, and FIG. 9 has a specific corresponding configuration between the ear tip and the housing, the ear tip according to the present disclosure may be designed to be adapted to any other kind of housing, and is not limited to the structure disclosed therein.

Figure 18A:
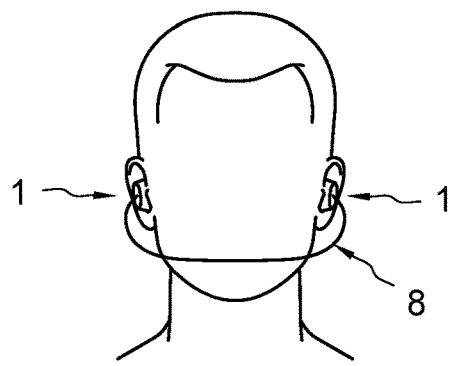
FIG. 18A illustrates a wearable device being used in accordance with some embodiments of the present disclosure.
Figure 18B:
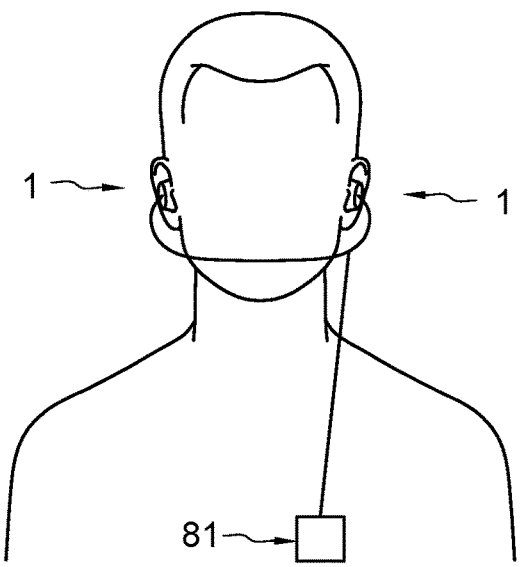
FIG. 18B illustrates a wearable device being used in accordance with some embodiments of the present disclosure.
Figure 18C:
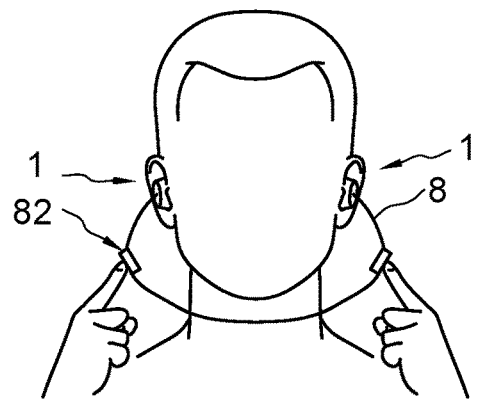
FIG. 18C illustrates a wearable device being used in accordance with some embodiments of the present disclosure.

FIG. 18A, FIG. 18B, and FIG. 18C illustrate a wearable device (such as the wearable device 1) being used in accordance with some embodiments of the present disclosure.

Referring to FIG. 18A, the left side and the right side of the wearable device 1 are connected through a wire or a cable 8. The electrical signals received from the left and right ear may be used to produce an ECG, or a heart rate variability (HRV).

Referring to FIG. 18B, an ECG patch 81 may be used in combination with the wearable device 1. The ECG patch 81 may be attached to the chest of a user. The ECG patch 81 and the wearable device 1 may be anatomical locations having potentials different enough to allow obtaining a good signal to noise ratio. The ECG patch 81 facilitate the collection of the electrical signals which may be sued to produce an ECG or HRV. In some embodiments, there may be a plurality of ECG patches used in combination with a multi-function wearable device (e.g., the wearable device 1B of FIG. 9).

Referring to FIG. 18C, an ECG patch 82 may be used in combination with the wearable device 1. For example, a left hand and/or a right hand of a user may be anatomical locations used in combination with the wearable device 1. The ECG patch 82 facilitate the collection of the electrical signals which may be sued to produce an ECG or HRV.

Figure 19A:
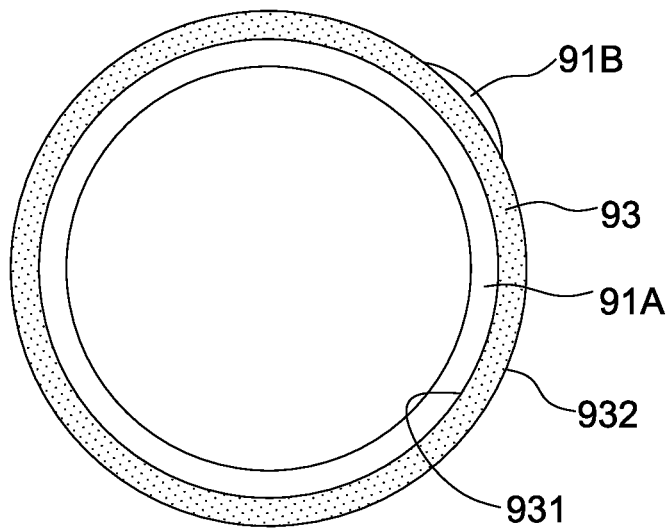
FIG. 19A illustrates a cross-sectional view of a wristband in accordance with some embodiments of the present disclosure.

Referring to FIG. 19A, FIG. 19A illustrates a cross-sectional view of a wristband 9 in accordance with some embodiments of the present disclosure. The wristband 9 includes a conductive layer 91A, a conductive element 91B, and an insulation element 93. The conductive element 91A may include a material similar to the first element 21. The conductive element 91B may include a material similar to the first element 21. The insulation element 93 may include a material similar to the insulation element 23.

As shown in FIG. 19A, the conductive element 91A is surrounded by the insulation element 93. In some embodiments, the conductive element 91A may be in contact with an inner surface 931 of the insulation element 93. The conductive element 91B may be disposed on an outer surface 932 of the insulation element 93. The conductive element 91A may be used to collect one or more bio-signals associated with the user of the wristband 9. When the wristband 9 is worn by the user, the conductive element 91A may be in contact with the user's skin to collect the bio-signals (e.g., electrical signals) from the user. The conductive element 91B may be used to collect one or more bio-signals associated with the user of the wristband 9. When the wristband 9 is worn by the user, for example, on the left hand, the user's right hand may touch the conductive element 91B to form a complete electrical transmission path among the conductive element 91A, the user's left hand, the user's body, the user's right hand, and the conductive element 91B, and a wristband processor (not shown in drawings). The wristband 9 may collect the bio-signals of the user, for example, ECG signals, a heart rate variability (HRV) or bioelectrical impedance analysis (BIA) signals.

Figure 19B:
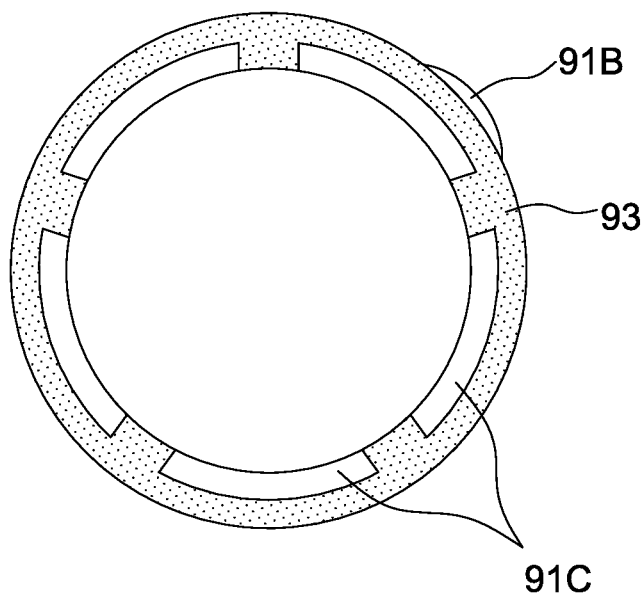
FIG. 19B illustrates a cross-sectional view of a wristband in accordance with some embodiments of the present disclosure.

Referring to FIG. 19B, it illustrates a cross-sectional view of a wristband 9A in accordance with some embodiments of the present disclosure. The wristband 9A of FIG. 19B is similar to the wristband 9 of FIG. 19A, and the differences therebetween are described below.

The wristband 9A includes a plurality of conductive elements 91C surrounded by the insulation element 93. The conductive elements 91C are spaced apart from each other by the insulation element 93. Different layers of the conductive elements 91C may be used to collect different bio-signals associated with the user of the earpiece. In some embodiments, the conductive elements 91C may be used to obtain different electrical signals which represent different bio-signals of the user. The category of the bio-signals is discussed the previous paragraphs and is not repeated here.

The positions and the numbers of the conductive layers and the conductive elements in the wristband 9A illustrated in the figures are for illustrative purpose only, and are not intended to limit the present disclosure. For example, there may be any number of conductive layers in the wristband 9A based on design requirements. For example, the conductive layers in the wristband 9A may be arranged in any position based on design requirements.

Spatially relative terms, such as "beneath," "below," "lower," "above," "upper," "left," "right" and the like, may be used herein for ease of description to describe one element or feature's relationship to another element(s) or feature(s) as illustrated in the figures. The spatially relative terms are intended to encompass different orientations of the device in use or operation, in addition to the orientation depicted in the figures. The apparatus may be otherwise oriented (rotated 90 degrees or at other orientations) and the spatially relative descriptors used herein may likewise be interpreted accordingly. It should be understood that when an element is referred to as being "connected to" or "coupled to" another element, it may be directly connected to or coupled to the other element, or intervening elements may be present.

As used herein, the terms "approximately", "substantially", "substantial" and "about" are used to describe and account for small variations. When used in conduction with an event or circumstance, the terms can refer to instances in which the event or circumstance occurs precisely as well as instances in which the event or circumstance occurs to a close approximation. As used herein with respect to a given value or range, the term "about" generally means within ±10%, ±5%, ±1%, or ±0.5% of the given value or range. Ranges can be expressed herein as from one endpoint to another endpoint or between two endpoints. All ranges disclosed herein are inclusive of the endpoints unless specified otherwise. The term "substantially coplanar" can refer to two surfaces within micrometers (μm) of lying along the same plane, such as within 10 μm, within 5 μm, within 1 μm, or within 0.5 μm of lying along the same plane. When referring to numerical values or characteristics as "substantially" the same, the term can refer to the values lying within ±10%, ±5%, ±1%, or ±0.5% of an average of the values.

The foregoing outlines features of several embodiments and detailed aspects of the present disclosure. The embodiments described in the present disclosure may be readily used as a basis for designing or modifying other processes and structures for carrying out the same or similar purposes and/or achieving the same or similar advantages of the embodiments introduced herein. Such equivalent constructions do not depart from the spirit and scope of the present disclosure, and various changes, substitutions, and alterations may be made without departing from the spirit and scope of the present disclosure.

What is claimed is:

1. A wearable device, comprising:
a first element configured to sense a bio-signal from a user; and
a second element configured to transmit the bio-signal to a processor;
wherein the second element has a first surface and a second surface non-coplanar with the first surface, and wherein the first element is in contact with the first surface and the second surface of the second element,
wherein the first surface and the second surface of the second element face each other,
wherein the first element includes a central portion and a tail portion extending from the central portion, wherein the central portion includes a plurality of stripe elements and the tail portion includes a plurality of sectorial elements.

2. The wearable device of claim 1, wherein one of the plurality of sectorial elements of the first element is substantially radially aligned with one of the plurality of stripe elements of the first element.

3. The wearable device of claim 1, wherein the plurality of sectorial elements of the first element are radially separated from the plurality of stripe elements of the first element.

4. The wearable device of claim 1, further comprising an insulation element separating the plurality of sectorial elements of the first element.

5. The wearable device of claim 4, wherein the insulation element separates the plurality of stripe elements of the first element.

6. The wearable device of claim 4, wherein the second element includes a plurality of stripe elements and a plurality of sectorial elements.

7. The wearable device of claim 6, wherein one of the plurality of sectorial elements of the second element is substantially radially aligned with one of the plurality of stripe elements of the second element.

8. The wearable device of claim 7, wherein the plurality of sectorial elements of the second element are radially separated from the plurality of stripe elements of the second element.

9. The wearable device of claim 6, wherein the second element includes a plurality of conductive pads connected to the plurality of strip elements, wherein the insulation element separates the plurality of conductive pads of the second element.

10. The wearable device of claim 1, further comprising an insulation element covering the first element, wherein the central portion of the first element is embedded in the insulation element.

11. A wearable device, comprising:
an insulation element including a plurality of first sectorial elements;
a flexible conductive element connected to the insulation element and configured to fit a user's skin, wherein the flexible conductive element includes a plurality of second sectorial elements interleaved with the plurality of first sectorial element; and
a conductive element including a first portion embedded in the insulation element and a second portion embedded in the flexible conductive element,
wherein the conductive element is configured to receive a signal from the flexible conductive element, and
wherein the conductive element has a first surface and a second surface opposite to the first surface, and the first surface and the second surface are encapsulated by the flexible conductive element.

12. The wearable device of claim 11, wherein the conductive element includes a conductive pad, wherein the first portion of the conductive element extends in the insulation element and contacts the conductive pad, wherein the second portion is separated from the conductive pad.

13. The wearable device of claim 11, wherein the first portion of the conductive element directly contacts the insulation element, and the second portion of the conductive element directly contacts the flexible conductive element.

14. The wearable device of claim 11, wherein the second portion of the conductive element includes a plurality of third sectorial elements, wherein the plurality of third sectorial elements interleaved with the plurality of first sectorial element.

15. The wearable device of claim 14, wherein an area of one of the plurality of third sectorial elements of the second portion of the conductive element is less than an area of one of the plurality of second sectorial element of the flexible conductive element.

16. A wearable device, comprising:
an ear tip, comprising:
a flexible conductive element;
a conductive element embedded in the flexible conductive element; and
an insulation element surrounding the flexible conductive element, and
a housing comprising a first conductive pad, wherein the first conductive pad is configured to receive a signal from the flexible conductive element through the conductive element,
wherein the conductive element is exposed by the flexible conductive element and directly contacts the housing,
wherein the flexible conductive element is physically separated from the housing by the insulation element, wherein the insulation element includes a first portion and a second portion, wherein the first portion, the flexible conductive element, the conductive element, and the second portion are arranged in sequence in a radial direction, wherein the conductive element includes a conductive pad exposed by the flexible conductive element, wherein the first portion of the insulation element is connected between the conductive pad and the flexible conductive element.

17. The wearable device of claim 16, wherein the flexible conductive element has a recess for accommodating the first portion of the insulation element.

\* \* \* \* \*